(12) United States Patent
Lukay et al.

(10) Patent No.: US 10,359,355 B2
(45) Date of Patent: Jul. 23, 2019

(54) HIGH TEMPERATURE FLUID SAMPLE AGING CELL

(71) Applicants: Richard F. Lukay, Houston, TX (US); John D. Norwood, Houston, TX (US)

(72) Inventors: Richard F. Lukay, Houston, TX (US); John D. Norwood, Houston, TX (US)

(73) Assignee: OFI Testing Equipment, Inc., Houston, TX (US)

( * ) Notice: Subject to any disclaimer, the term of this patent is extended or adjusted under 35 U.S.C. 154(b) by 162 days.

(21) Appl. No.: 15/664,890

(22) Filed: Jul. 31, 2017

(65) Prior Publication Data
US 2017/0328829 A1 Nov. 16, 2017

Related U.S. Application Data

(63) Continuation of application No. 14/613,195, filed on Feb. 3, 2015, now Pat. No. 9,784,667.
(Continued)

(51) Int. Cl.
| | |
|---|---|
| *G01N 17/02* | (2006.01) |
| *G01N 19/00* | (2006.01) |
| *G01N 33/28* | (2006.01) |
| *B01L 3/00* | (2006.01) |
| *F16J 15/00* | (2006.01) |
| *F16J 15/08* | (2006.01) |

(Continued)

(52) U.S. Cl.
CPC ............ *G01N 19/00* (2013.01); *F16J 15/028* (2013.01); *F16J 15/0887* (2013.01); *G01N 17/002* (2013.01); *B01L 3/567* (2013.01); *B01L 2200/0689* (2013.01); *G01N 33/2823* (2013.01)

(58) Field of Classification Search
CPC .. G01N 17/002; G01N 19/00; G01N 33/2823; B01L 3/567; B01L 2200/0689; F16J 15/028; F16J 15/0887
See application file for complete search history.

(56) References Cited

U.S. PATENT DOCUMENTS

| | | |
|---|---|---|
| 2,780,483 A | 2/1957 | Kessler |
| 3,074,747 A | 1/1963 | Boughton |

(Continued)

OTHER PUBLICATIONS

Fann Instrument Company, 600° F. High Temperature Aging Cell Instruction Manual, Manual No. D00654827, Revision C, Jan. 2013, Instrument No. 102111608.

*Primary Examiner* — Randy W Gibson
(74) *Attorney, Agent, or Firm* — Keeling Law, LLC; Kenneth A. Keeling; Mark S. Solomon

(57) ABSTRACT

Exemplary embodiments of a high temperature aging cell provide a metal-to-metal fluid seal, and generally include a central tension post containing a flange having an inclined surface; and a seal ring concentrically arranged thereon, its outer circumference positioned at least partly intermediate the flange and the cell interior surface. In various embodiments, a thrust ring retains the seal ring; a thrust washer engages the thrust ring; a tension ring is attached to the tension post for biasing the thrust ring toward the flange; and an outer cap retains various components in relation to the aging cell. A pressure control device allows for pressure elevation.

Exemplary embodiments of a sample aging method generally include aging a liquid sample by sealing the sample in the cell via biasing of the seal ring into sealing engagement with an interior surface of the cell. Subsequent sample treatment may involve elevating its temperature and/or pressure.

20 Claims, 4 Drawing Sheets

Related U.S. Application Data

(60) Provisional application No. 61/936,718, filed on Feb. 6, 2014.

(51) Int. Cl.
*F16J 15/02* (2006.01)
*G01N 17/00* (2006.01)

(56) References Cited

U.S. PATENT DOCUMENTS

| | | |
|---|---|---|
| 3,289,467 A | 12/1966 | Parker et al. |
| 3,537,731 A | 11/1970 | Reddy |
| 3,752,509 A | 8/1973 | Stafford |
| 3,854,761 A | 12/1974 | David |
| 4,452,474 A | 6/1984 | Hagner |
| 4,529,231 A | 7/1985 | Greenawalt |
| 4,556,242 A | 12/1985 | Kowal et al. |
| 4,621,843 A | 11/1986 | Straub |
| 4,776,618 A | 10/1988 | Barree |
| 5,779,282 A | 7/1998 | Ezze |
| 8,230,747 B2 | 7/2012 | Lindeberg |
| 2009/0211364 A1 | 8/2009 | Lindeberg |
| 2013/0312511 A1 | 11/2013 | Jamison et al. |
| 2014/0319080 A1 | 10/2014 | Kaarigstad et al. |
| 2015/0354300 A1 | 12/2015 | Jamison et al. |
| 2016/0186745 A1 | 6/2016 | Roll |

HIGH TEMPERATURE FLUID SAMPLE AGING CELL

CROSS-REFERENCE TO RELATED APPLICATIONS

This application is a continuation of prior U.S. patent application Ser. No. 14/613,195, filed Feb. 3, 2015, which claims the benefit of U.S. Provisional Application No. 61/936,718, filed Feb. 6, 2014, which applications are both incorporated herein by reference as if reproduced in full below.

STATEMENT REGARDING FEDERALLY SPONSORED RESEARCH OR DEVELOPMENT

Not applicable.

FIELD OF THE DISCLOSURE

This invention relates generally to testing equipment used to measure properties of materials and chemical systems, and more specifically to an apparatus and method to subject materials to temperatures in excess of 100° C. while maintaining the materials in a liquid state.

BACKGROUND

In the oil and gas industry, it is necessary to understand the properties of materials used during drilling and exploration, and to determine how properties are affected by temperature, pressure, and time. Various aging cells are used to determine properties of materials during static temperature exposure or during a dynamic mode, such as in a roller oven. Typical aging cells are constructed of corrosion resistant metal and capable of achieving test temperatures of 600° F. (316° C.). Such aging cells typically involve the use of gaskets, o-rings, or other sealing means which are subject to degradation when exposed to elevated temperatures and/or pressures.

BRIEF SUMMARY OF THE DISCLOSURE

Embodiments of a high temperature aging cell generally provide a metal-to-metal fluid seal for retaining fluids within the cell; wherein, a central tension post is constructed with a flange having an inclined surface; a seal ring is concentrically arranged on the tension post, the seal ring having a seal extension at its outer circumference, the seal extension extending at least partially exterior of the inclined flange outer edge, and the seal extension positioned at least partly intermediate the inclined flange and an aging cell body interior surface; a thrust ring retaining the seal ring; a thrust washer engaging the thrust ring; a tension ring attached to the tension post for biasing the thrust ring toward the tension post flange; and an outer cap retaining the tension ring, thrust washer, thrust ring, and seal ring in relation to the aging cell body.

An embodiment of a method of the present invention comprises inserting a tension post, having a flange with an inclined surface, in an end of an aging cell, inserting a seal ring on the tension post flange, inserting a thrust ring on the seal ring, fixedly attaching a tension ring on the tension post, with the seal thrust ring and the seal ring intermediate the flange and the tension ring, and biasing the tension ring toward the flange until the seal ring sealingly engages the aging cell interior surface.

BRIEF DESCRIPTION OF THE DRAWINGS

For a more complete understanding of the exemplary embodiments, reference is now made to the following Detailed Description of Exemplary Embodiments of the Invention, taken in conjunction with the accompanying drawings, in which.

DETAILED DESCRIPTION OF EXEMPLARY EMBODIMENTS OF THE INVENTION

Figure 1:
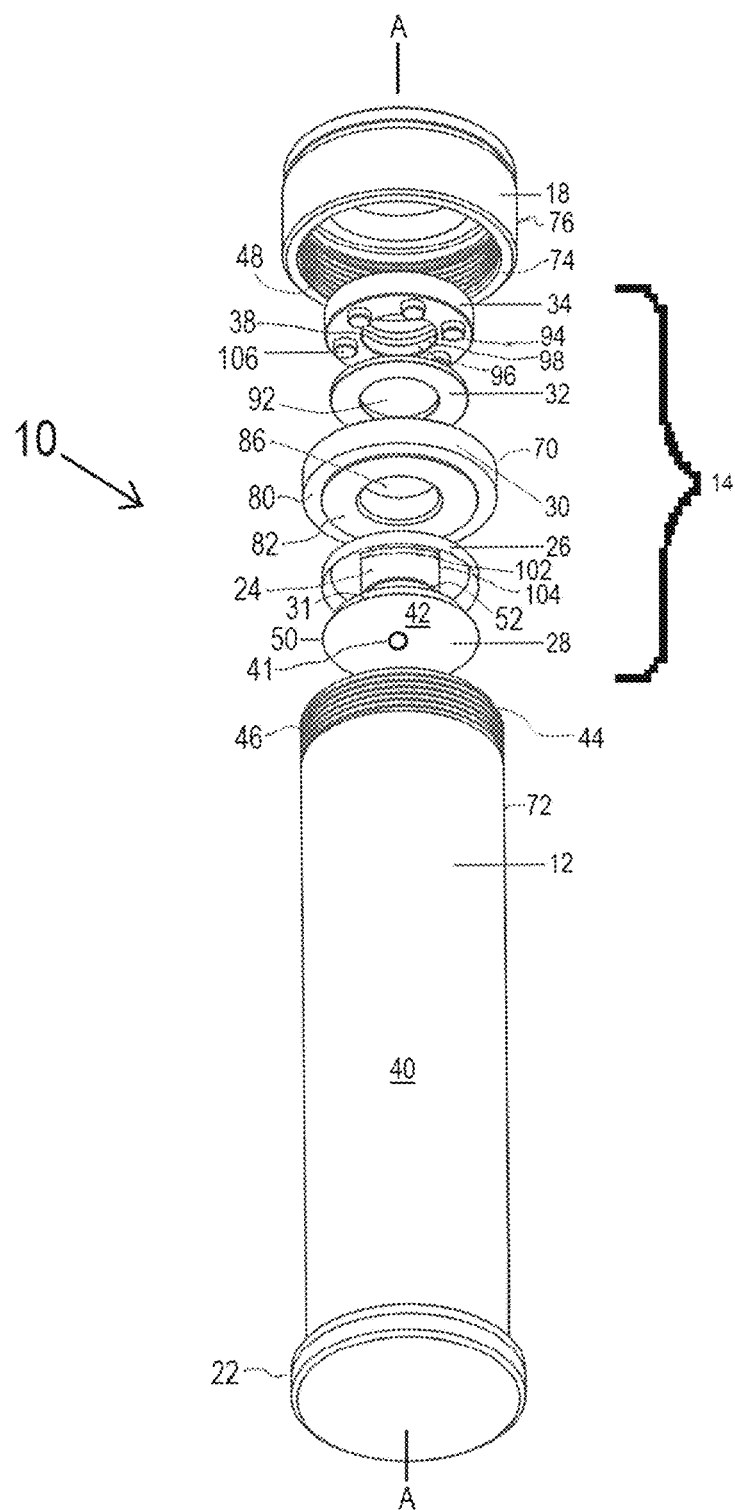
FIG. 1 depicts an exploded view of an aging cell of an embodiment of the present invention.

The exemplary embodiments are best understood by referring to the drawings, like numerals being used for like and corresponding parts of the various drawings. The directions lower and upper as used in this specification are used for descriptive purposes only and it will be understood by one having skill in the art that different orientations are possible.

As used herein inner or inward means toward the axial center A-A of the aging cell and outer or outward means away from axial center A-A, unless the context indicates a contrary meaning.

Referring to FIGS. 1 through 5, various details of an embodiment of the aging cell 10 of the present invention are depicted. In one embodiment, aging cell 10 comprises a cell body 12, a sealing assembly 14, a pressure control device, such as stem valve 16, and a cap 18. In other embodiments, the sealing assembly may comprise the cap as an integral component thereof. In certain embodiments where, for example, when external pressurization of the aging cell is not desired, the pressure control device may be omitted or replaced with a pressure relief device.

Still referring to FIG. 1, aging cell body 12 comprises an elongated hollow cylinder defined by a substantially annular body wall 40 and a closed lower end 22. Sealing assembly 14 fits within an open upper end 44 of cell body 12. Cap 18 is removably attachable to upper end 44 of cell body 12. In an exemplary embodiment, attachment of cap 18 to cell body 12 is achieved by cooperative engagement between cell body 12 exterior threading 46 and cap 18 interior threading 48.

In one embodiment, sealing assembly 14 comprises tension post 24, seal ring 26, thrust ring 30, thrust washer 32, and tension ring 34. Tension post 24 is a cylinder having an outwardly-extending flange 28 at its lower end. External threading 102 is provided at the upper end of tension post 24 for threading engagement of corresponding internal threading 96 of tension ring 34. An opening and threading (not shown in FIG. 1) is provided interior of tension post 24, such opening and threading configured to receive a pressure control device, such as stem valve 16. A base opening 41 of tension post 24 allows controlled pressurization and pressure release of the interior of aging cell 10 during operation.

Figure 2:
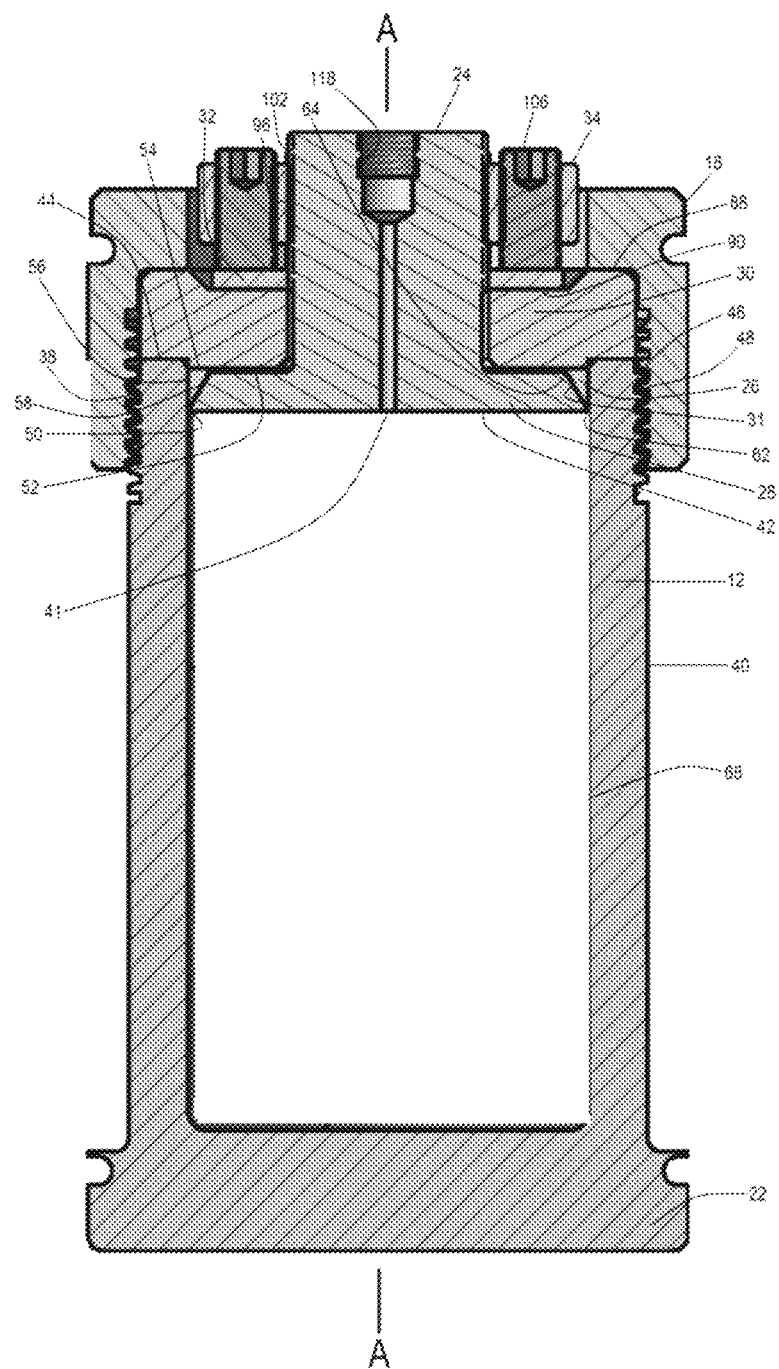
FIG. 2 depicts a cross-sectional view of an aging cell of an embodiment of the present invention.
Figure 3:
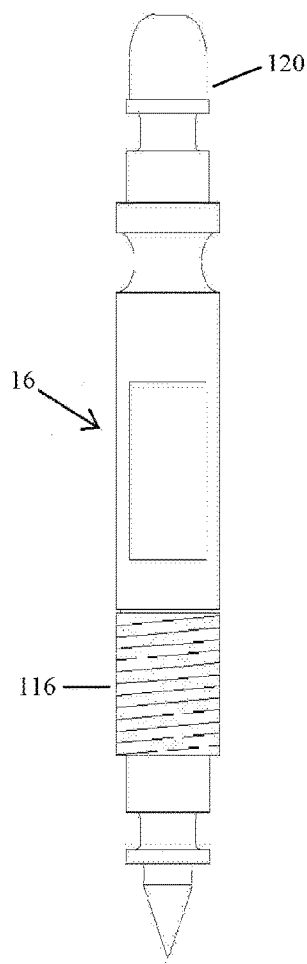
FIG. 3 depicts a stem valve.
Figure 4:
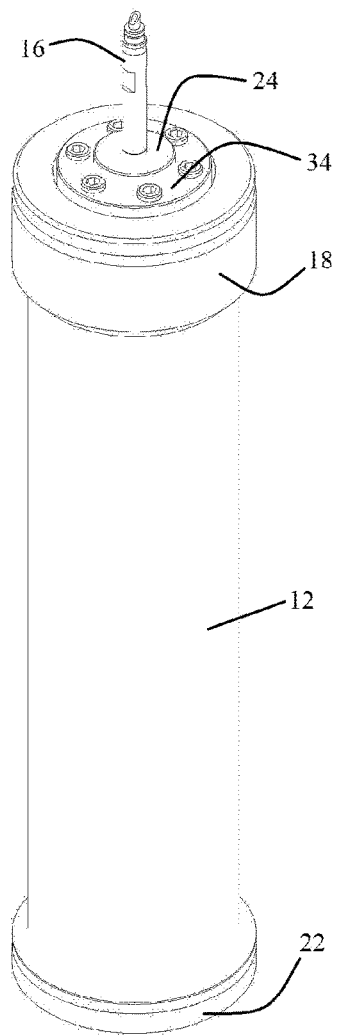
FIG. 4 depicts an assembled aging cell of an embodiment of the present invention.

Referring to FIG. 2, a detail of tension post flange 28 is depicted in relation to seal ring 26 and thrush washer 32. Tension post flange 28 has a beveled upper surface 31 extending circumferentially around flange 28. Surface 31 is inclined at an acute angle in relation to cell wall 40 and is inclined at an acute angle in relation to flange lower surface 42. Particularly, beveled surface 31 extends from an outermost edge 50 of lower surface 42, upwardly and inwardly, towards flange upper surface location 52 proximate tension post 24.

Seal ring 26 is a circular ring constructed with a substantially horizontal upper surface 54, a substantially vertical outer surface 56, and an inclined inner surface 58. Inner surface 58, from lower edge 62 of outer surface 56 to inner edge 64 of upper surface 54 is inclined at an acute angle to outer surface 56 and at an acute angle to upper surface 54. Inclined inner surface 58 is sized and constructed for sliding engagement with beveled edge 31.

Outer surface 56 is constructed and sized to slide within inner surface 68 of cell wall 40. Outer surface 56 is further sized and constructed to have a larger circumference than outermost edge 50 of lower surface 42 of flange 28. Seal ring 26 is sized and constructed such that upper surface 54 of seal ring 26 is elevated in relation to upper surface location 52 of flange 28.

Still referring to FIG. 2, thrust ring 30 is a substantially circular ring having an axial center opening 86. Thrust ring 30 is sized and constructed to have a substantially vertical outer edge 70 that extends proximate outer surface 72 of wall 40. The circumference of outer surface 72 is less than inner surface 74 of cap 18 to allow cap 18 wall 76 to extend outside outer surface 72. Thrust ring 30 has a lower surface 80 extending horizontally inward from outer surface 72. Lower surface 80 is sized and constructed to rest on wall 40 upper end 44. A horizontal lower surface extension 82 of lower surface 80 extends below lower surface 80. Lower surface extension 82 extends below and parallel to lower surface 80. Lower surface extension 82 extends horizontally from cell wall inner surface 68 to center opening 86. Lower surface extension 82 is sized and constructed to extend below upper end 44 of cell wall 40 and is further sized and constructed to engage upper surface 54 of seal ring 26.

Upper surface 88 of thrust ring 30 extends horizontally. A countersunk washer surface 90 is provided in upper surface 88. Washer surface 90 is sized and constructed to receive a thrust washer 32. Thrust washer 32 is a washer structure having a central opening 92.

Tension ring 34 is a substantially hollow cylinder having a central opening 94. Threading 96 is provide on interior wall 98 of tension ring 34 proximate central opening 94 for threading engagement of corresponding tension post threading 102 provided on exterior surface 104 of tension post 24. Accordingly, tension ring 34 may be removably attached to tension post 24 by threaded attachment.

One or more bias adjustment devices are provided for biasing various components of sealing assembly 14 against each other. In one embodiment, a plurality of set screws 106 extend vertically through tension ring 34. Set screws 106 are sized and constructed to engage thrust washer 32. Tension ring 34, thrust washer 32, thrust ring 30, and seal ring 26 are all concentrically arranged along axis A-A. Downward biasing of set screws 106 results in corresponding bias of thrust washer 32 against thrust ring 30 and in corresponding bias of thrust ring 30 against seal ring 26. Such bias forces seal ring 26 downward in relation to flange 28 and forces lower edge 62 outward toward inner surface 68 of cell wall 40. Accordingly, seal system 14 may be operated to bias thrust ring 30 downward toward flange 28, and thereby force seal ring 26 into a sealed position wherein lower edge 62 and at least a portion of outer surface 56 of seal ring 26 sealingly engage inner surface 68 of cylinder wall 40. The biasing of lower edge 62 and a portion of outer surface 56 against inner surface 68 constitutes a seal extension of seal ring 26.

In various embodiments of the present invention, components of seal system 14, cap 18, and/or cell body 12 may comprise any suitable material, including but not limited to, various metals and/or metal alloys. In an exemplary embodiment of the present invention, cell 12, tension post 24, flange 28, thrust ring 30, and seal ring 26 are constructed of corrosion resistant metal, such as but not limited to, stainless steel. Accordingly, an aging cell having metal interior components is provided.

A pressure control device is utilized to provide a determined pressure to the interior of aging cell 10. In one embodiment, a valve stem 16 is employed as the pressure control device. Valve stem 16 may be a commercially-available valve having lower connecting threading 116 for threaded connection to central opening threading 118 of tension post 24. In other embodiments, valve stem 16 is attachable to cap 18. Valve stem 16 is provided with an upper connector 120 at its upper end for connection to a pressure source (not shown). Valve stem 16 is constructed to provide selective fluid communication into and out of cell 12 through tension post base opening 41. In an exemplary embodiment, valve stem 16 is a commercially available stem valve such as a stem valve manufactured and marketed by OFI Testing Equipment, Inc., Houston, Tex., as Part No. 175-16.

In one embodiment, aging cell 10 is adapted to be operated at temperatures up to about 600° F. (316° C.) and pressures up to about 2,000 PSI (13.8 MPa). Elevating the temperature of aging cell 10, and a test sample contained therein, may be accomplished by various means as are known in the art. In one embodiment, heating of aging cell 10 containing a test sample is accomplished in an oven, such as a roller oven.

Operation

In operation, a test sample (not shown) is placed in test cell (cell body) 12. In one embodiment, the sample comprises one or more liquids. In one embodiment, the components of sealing assembly 14 are provided in the appropriate orientation and connectively restrained together by cooperative engagement of tension post 24 exterior threading 102, and tension ring 34 internal threading 38. Valve stem 16 is inserted into tension post 24 and connected thereto by cooperative engagement of valve stem 16 external threading 116 and tension post 24 internal threading 118. Sealing assembly 14, along with connected valve stem 16, is inserted into the open upper end 44 of test cell 12 until thrust ring 30 engages upper end 44. Outer cap 18 is attached to cell 12 by cooperative engagement of cap 18 internal threading 48 and cell body 12 exterior threading 46. Set screws 106 are tightened to a determined torque to bias thrust ring 30 lower surface extension 82 against seal ring 26, thereby biasing seal ring 26, at lower edge 62, into a sealed position in relation to cell wall 40 inner surface 68. Such biasing is accomplished at the interface of flange 28 beveled surface 31 with seal ring 26 inclined inner surface 58, as inner surface 58 moves downward in relation to beveled surface 31.

In operation and upon pressurization of a fluid within test cell 12, the fluid pressure additionally biases flange 28 upward, thereby creating additional force to bias seal ring 26 outward in a sealed position in relation to cell wall 40 inner surface 68.

Figure 5:
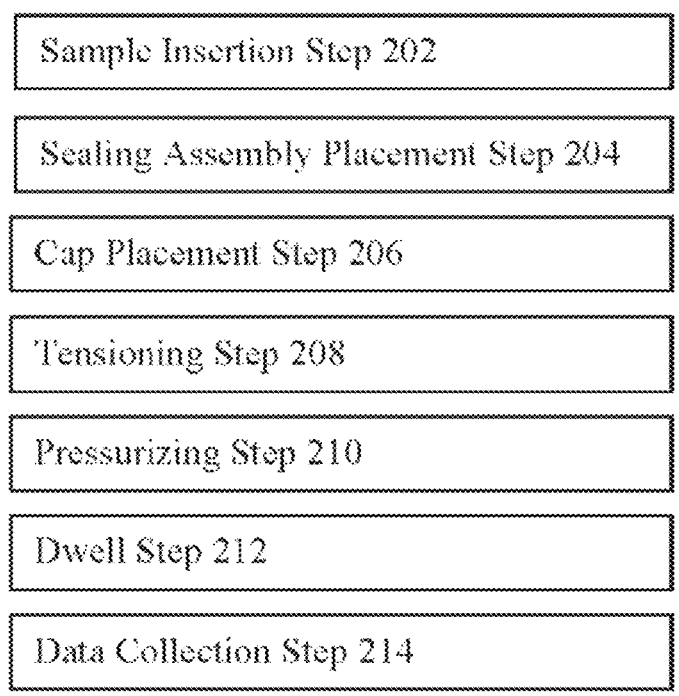
FIG. 5 depicts an embodiment of a method of the present invention.

Referring to FIG. 5, an exemplary test method 200 of the present invention comprises:

A sample insertion step 202 comprising inserting a sample to be tested in a test cell, such as test cell 12.

A sealing assembly placement step 204 comprising inserting a sealing assembly, such as sealing assembly 14, comprising tension post 24, seal ring 26, thrust ring 30, thrust washer 32, and tension ring 34, and valve stem 16, in a test cell such as test cell 12.

A cap placement step 206 comprising attaching a cap, such as cap 18, to the test cell such that cap 18 at least partially retains the sealing assembly within the test cell.

A tensioning step 208 comprising applying torque to tension a bias adjustment device, such as set screws 106, to bias a thrust ring, such as thrust ring 30, toward a flange, such as flange 28, and correspondingly bias at least a portion of a seal ring, such as seal ring 26, to a sealing position in relation to the inner test cell wall.

A pressurizing step 210 comprising introducing controlled pressure to the test cell.

A dwell step 212 comprising maintaining the test cell at a controlled temperature and pressure during a determined time interval.

A data collection step 214 comprising obtaining test sample data.

In operation and upon pressurization of a fluid within test cell 12, the fluid pressure additionally biases flange 28 upward, thereby creating additional force to bias seal ring 26 outward in a sealed position in relation to cell wall 40 inner surface 68.

Various embodiments will be understood from the foregoing description, and it will be apparent that, although embodiments have been described in detail, various changes, substitutions, and alterations may be made in the manner, procedure and/or details thereof without departing from the spirit and scope or sacrificing any of its material advantages, the forms hereinbefore described being merely exemplary embodiments thereof.

We claim:

1. An apparatus comprising:
   a test cell comprising:
      a cell body comprising a hollow, substantially cylindrical vessel having a transverse opening at an end thereof; and
      a sealing assembly at least partially insertable into said cell body via said opening, said sealing assembly comprising:
         a central tension post comprising a flange having an inclined surface; and
         a seal ring disposed concentrically around a portion of said tension post; wherein:
         said sealing assembly biases said seal ring against said inclined surface; and
         at least a portion of said seal ring extends outwardly beyond an outer edge of said flange and engages an interior surface of said cell body in fluidly sealing said cell body.

2. The apparatus of claim 1, wherein said seal ring comprises:
   a substantially planar upper surface;
   a substantially planar outer surface; and
   a substantially planar inner surface;
      wherein:
         said seal ring upper surface is oriented substantially parallel to a lower surface of said flange;
         said seal ring outer surface is oriented substantially perpendicular to said seal ring upper surface; and
         said seal ring inner surface is beveled.

3. The apparatus of claim 1, wherein liquid sample is introducible into said test cell only through said cell body opening.

4. The apparatus of claim 1, wherein, in fluidly sealing said cell body, said seal ring contacts only one flange.

5. The apparatus of claim 1, wherein said seal ring comprises metal.

6. The apparatus of claim 1, wherein said apparatus comprises only metallic components.

7. An apparatus comprising:
   a test cell comprising:
      a cell body comprising a hollow, substantially cylindrical vessel having a transverse opening at an end thereof;
      a sealing assembly at least partially insertable into said cell body via said opening, said sealing assembly comprising:
         a central tension post comprising a flange having an inclined surface; and
         a seal ring disposed concentrically around a portion of said tension post;
         a thrust ring; and
         a tension ring; and
      a cap;
         wherein:
            said tension ring biases said thrust ring against said seal ring;
            said seal ring is disposed intermediate said thrust ring and said flange;
            said sealing assembly biases said seal ring against said inclined surface;
            at least a portion of said seal ring extends outwardly beyond an outer edge of said flange and engages an interior surface of said cell body in fluidly sealing said cell body; and
            said cap engages said cell body and retains said sealing assembly in relation to said cell body.

8. The apparatus of claim 7, comprising a pressure control device.

9. The apparatus of claim 8, wherein said pressure control device comprise a valve stem.

10. The apparatus of claim 7, comprising a bias adjustment device that biases said seal ring against said flange inclined surface.

11. The apparatus of claim 10, wherein said bias adjustment device comprises one or more set screws.

12. The apparatus of claim 7, wherein said tension ring is removably connectable to said tension post.

13. The apparatus of claim 7, comprising a thrust washer disposed intermediate said tension ring and said thrust ring.

14. A method of aging a sample in a test cell, comprising:
   providing a cell body containing said sample, said sample comprising one or more liquids, wherein said cell body comprises a hollow, substantially cylindrical vessel having a transverse opening at an end thereof;
   inserting at least partially into said cell body a sealing assembly, wherein said sealing assembly comprises:
      a central tension post comprising a flange having an inclined surface; and
      a seal ring disposed concentrically around a portion of said tension post;
   manipulating said sealing assembly such that said seal ring is biased against said inclined surface, whereby at least a portion of said seal ring extends outwardly beyond an outer edge of said flange and engages an interior surface of said cell body to fluidly seal said cell body; and exposing said sample to a condition selected from the group consisting of:
elevated pressure;
elevated temperature;
both elevated pressure and elevated temperature.

15. The method of claim 14, wherein said sealing assembly comprises a thrust ring disposed such that said seal ring is disposed intermediate said thrust ring and said flange.

16. The method of claim 15, wherein said sealing assembly comprises a tension ring that biases said thrust ring against said seal ring.

17. The method of claim 16, wherein said sealing assembly comprises a thrust washer disposed intermediate said tension ring and said thrust ring.

18. The method of claim 14, comprising attaching a cap to said cell body, wherein said cap engages said cell body and retains said sealing assembly in relation to said cell body.

19. The method of claim 14, comprising fluidly connecting a pressure control device, directly or indirectly, to said test cell.

20. The method of claim 19, wherein said pressure control device comprise a valve stem.

* * * * *